US010569011B2

(12) United States Patent
Dilanni et al.

(10) Patent No.: US 10,569,011 B2
(45) Date of Patent: *Feb. 25, 2020

(54) FLUID DELIVERY DEVICE, TRANSCUTANEOUS ACCESS TOOL AND INSERTION MECHANISM FOR USE THEREWITH

(71) Applicant: Insulet Corporation, Bedford, MA (US)

(72) Inventors: Steven Dilanni, Danvers, MA (US); Ian McLaughlin, Boxborough, MA (US); Jason Brian O'Connor, South Boston, MA (US); Robert Campbell, Waltham, MA (US); Kevin Schmid, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/194,873

(22) Filed: Nov. 19, 2018

(65) Prior Publication Data

US 2019/0255251 A1 Aug. 22, 2019

Related U.S. Application Data

(63) Continuation of application No. 13/854,445, filed on Apr. 1, 2013, now Pat. No. 10,130,758, which is a
(Continued)

(51) Int. Cl.
*A61M 5/145* (2006.01)
*A61B 5/145* (2006.01)
(Continued)

(52) U.S. Cl.
CPC ..... *A61M 5/14566* (2013.01); *A61B 5/14532* (2013.01); *A61B 5/14865* (2013.01);
(Continued)

(58) Field of Classification Search
CPC .......... A61M 5/14566; A61M 5/14244; A61M 5/1452; A61M 5/158; A61M 5/1723; A61B 5/14532; A61B 5/14865
See application file for complete search history.

(56) References Cited

U.S. PATENT DOCUMENTS 5,261,884 A 11/1993 Stern et al.
5,503,628 A 4/1996 Fetters et al.
(Continued)

FOREIGN PATENT DOCUMENTS

EP 2397181 12/2011
EP 2830499 10/2013
(Continued)

OTHER PUBLICATIONS

EPO Search Report dated Nov. 11, 2015, received in corresponding Application No. 13768938.6, 7 pgs.
(Continued)

*Primary Examiner* — Imani N Hayman
*Assistant Examiner* — Tiffany Legette

(57) ABSTRACT

A fluid delivery device comprising a fluid reservoir; a transcutaneous access tool fluidly coupled to the fluid reservoir, the transcutaneous access tool including a needle or a trocar; and a transcutaneous access tool insertion mechanism for deploying the transcutaneous access tool, wherein the insertion mechanism is configured to insert and retract the needle/trocar in a single, uninterrupted motion.

22 Claims, 5 Drawing Sheets

Related U.S. Application Data continuation of application No. PCT/US2013/034674, filed on Mar. 29, 2013.

(60) Provisional application No. 61/618,028, filed on Mar. 30, 2012.

(51) Int. Cl.
| | |
|---|---|
| *A61B 5/1486* | (2006.01) |
| *A61M 5/142* | (2006.01) |
| *F04B 9/02* | (2006.01) |
| *A61M 5/172* | (2006.01) |
| *A61M 5/158* | (2006.01) |
| *A61M 5/32* | (2006.01) |
| *A61M 5/14* | (2006.01) |

(52) U.S. Cl.
CPC ...... *A61M 5/1452* (2013.01); *A61M 5/14244* (2013.01); *A61M 5/14248* (2013.01); *A61M 5/158* (2013.01); *A61M 5/1723* (2013.01); *F04B 9/02* (2013.01); *A61M 5/3291* (2013.01); *A61M 2005/1403* (2013.01); *A61M 2005/14252* (2013.01); *A61M 2005/14506* (2013.01); *A61M 2230/201* (2013.01); *F04C 2270/041* (2013.01)

(56) References Cited

U.S. PATENT DOCUMENTS

| | | | |
|---|---|---|---|
| 7,018,360 | B2 | 3/2006 | Flaherty et al. |
| 7,128,727 | B2 | 10/2006 | Flaherty et al. |
| 7,144,384 | B2 | 12/2006 | Gorman |
| 9,402,950 | B2 | 8/2016 | DiIanni et al. |
| 2002/0032374 | A1 | 3/2002 | Holker et al. |
| 2003/0163097 | A1 | 8/2003 | Fleury et al. |
| 2004/0010207 | A1 | 1/2004 | Flaherty et al. |
| 2004/0064088 | A1 | 4/2004 | Gorman et al. |
| 2004/0092865 | A1 | 5/2004 | Flaherty et al. |
| 2005/0020980 | A1 | 1/2005 | Inoue et al. |
| 2005/0203461 | A1 | 9/2005 | Flaherty et al. |
| 2005/0238507 | A1 | 10/2005 | DiIanni et al. |
| 2006/0155210 | A1 | 7/2006 | Beckman et al. |
| 2006/0178633 | A1 | 8/2006 | Garibotto et al. |
| 2006/0253085 | A1 | 11/2006 | Geismar et al. |
| 2006/0282290 | A1 | 12/2006 | Flaherty et al. |
| 2007/0005018 | A1 | 1/2007 | Tekbuchava |
| 2007/0118405 | A1 | 5/2007 | Campbell et al. |
| 2007/0282269 | A1 | 12/2007 | Carter et al. |
| 2008/0004515 | A1 | 1/2008 | Jennewine |
| 2008/0051738 | A1 | 2/2008 | Griffin |
| 2009/0062767 | A1 | 3/2009 | Van Antwerp et al. |
| 2009/0198215 | A1 | 8/2009 | Chong et al. |
| 2010/0152658 | A1 | 6/2010 | Hanson et al. |
| 2011/0054399 | A1 | 3/2011 | Chong et al. |
| 2011/0230833 | A1 | 9/2011 | Landman et al. |
| 2012/0078161 | A1 | 3/2012 | Masterson et al. |
| 2014/0127048 | A1 | 5/2014 | DiIanni et al. |
| 2014/0128839 | A1 | 5/2014 | DiIanni et al. |
| 2014/0142508 | A1 | 5/2014 | DiIanni et al. |
| 2017/0128664 | A1 | 5/2017 | DiIanni et al. |

FOREIGN PATENT DOCUMENTS

| | | |
|---|---|---|
| WO | 9856293 | 12/1998 |
| WO | 2008133702 | 11/2008 |
| WO | 2013149186 | 10/2013 |

OTHER PUBLICATIONS

PCT International Search Report and Written Opinion dated Aug. 6, 2013, received in corresponding PCT Application No. PCT/US13/34674, pp. 1-19.
International Preliminary Report on Patentability dated Oct. 9, 2014, issued in PCT Patent Application No. PCT/US2013/034674, 15 pages.
Office Action dated Mar. 31, 2015, issued in U.S. Appl. No. 13/854,456, 11 pages.
U.S. Office Action dated Aug. 4, 2015, issued in U.S. Appl. No. 13/854,463 11 pages.
U.S. Office Action dated Sep. 23, 2015, issued in U.S. Appl. No. 13/854,456, 13 pages.
Notice of Allowance dated Mar. 25, 2016, issued in U.S. Appl. No. 13/854,456, 9 pages.
U.S. Office Action dated May 17, 2016, issued in U.S. Appl. No. 13/854,445, 11 pages.
U.S. Office Action dated May 31, 2016, issued in U.S. Appl. No. 13/854,463, 16 pages.
U.S. Office Action dated Jan. 25, 2017, issued in U.S. Appl. No. 13/854,445, 23 pages.
U.S. Office Action dated Mar. 3, 2017, issued in U.S. Appl. No. 13/854,463, 12 pages.
U.S. Office Action dated Oct. 31, 2017, issued in U.S. Appl. No. 13/854,445, 15 pages.
U.S. Office Action dated Oct. 31, 2017, issued in U.S. Appl. No. 13/854,463 13 pages.
Notice of Allowance dated May 21, 2018, issued in U.S. Appl. No. 13/854,463, 7 pages.
Notice of Allowance dated May 23, 2018, issued in U.S. Appl. No. 13/854,445, 8 pages.

FLUID DELIVERY DEVICE, TRANSCUTANEOUS ACCESS TOOL AND INSERTION MECHANISM FOR USE THEREWITH

CROSS-REFERENCE TO RELATED APPLICATIONS

This application is a continuation of U.S. Non-Provisional application Ser. No. 13/854,445 filed Apr. 1, 2013, now U.S. Pat. No. 10,130,758, which is a continuation of PCT Application Serial No. PCT/US13/34674 filed Mar. 29, 2013 and claims the benefit of U.S. Provisional Application Ser. No. 61/618,028, filed Mar. 30, 2012, the teachings of which are incorporated herein by reference.

TECHNICAL FIELD

The present invention relates to fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump, to improve the comfort to the user, and/or to incorporate continuous glucose monitoring (CGM). These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously. In certain embodiments the fluid delivery device may comprise an ambulatory insulin infusion device to administer insulin to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, the transcutaneous access tool includes a needle/trocar, and the transcutaneous access tool insertion mechanism is configured to insert and retract the needle/trocar in a single, uninterrupted motion. In such a manner, the pain of insertion and retraction of the needle/trocar experienced by the patient may be reduced.

In certain embodiments, the fluid delivery device may comprise a fluid reservoir; a transcutaneous access tool fluidly coupled to the fluid reservoir, the transcutaneous access tool including a needle/trocar; and a transcutaneous access tool insertion mechanism for deploying the transcutaneous access tool, wherein the insertion mechanism is configured to insert and retract the needle/trocar in a single, uninterrupted motion.

In certain embodiments, the fluid delivery device may comprise a fluid reservoir; a transcutaneous access tool fluidly coupled to the fluid reservoir, the transcutaneous access tool including at least a needle/trocar; and a transcutaneous access tool insertion mechanism for deploying the transcutaneous access tool, wherein the insertion mechanism is configured to insert the needle/trocar with an increasing insertion force as the needle/trocar moves in an insertion direction.

In certain embodiments, the transcutaneous access tool insertion mechanism for deploying a transcutaneous access tool including a cannula and a needle/trocar located inside of the cannula may comprise a first sliding member configured to move the needle/trocar in an insertion direction and a retraction direction; a second sliding member configured to move the cannula in the insertion direction; a torsion spring; and linkages coupled between the torsion spring and the first sliding member such that energy stored in the torsion spring causes the linkages to move the first sliding member in the insertion direction and the retraction direction.

BRIEF DESCRIPTION OF THE DRAWINGS

These and other features and advantages will be better understood by reading the following detailed description, taken together with the drawings wherein.

DETAILED DESCRIPTION

Figures 1, 2:
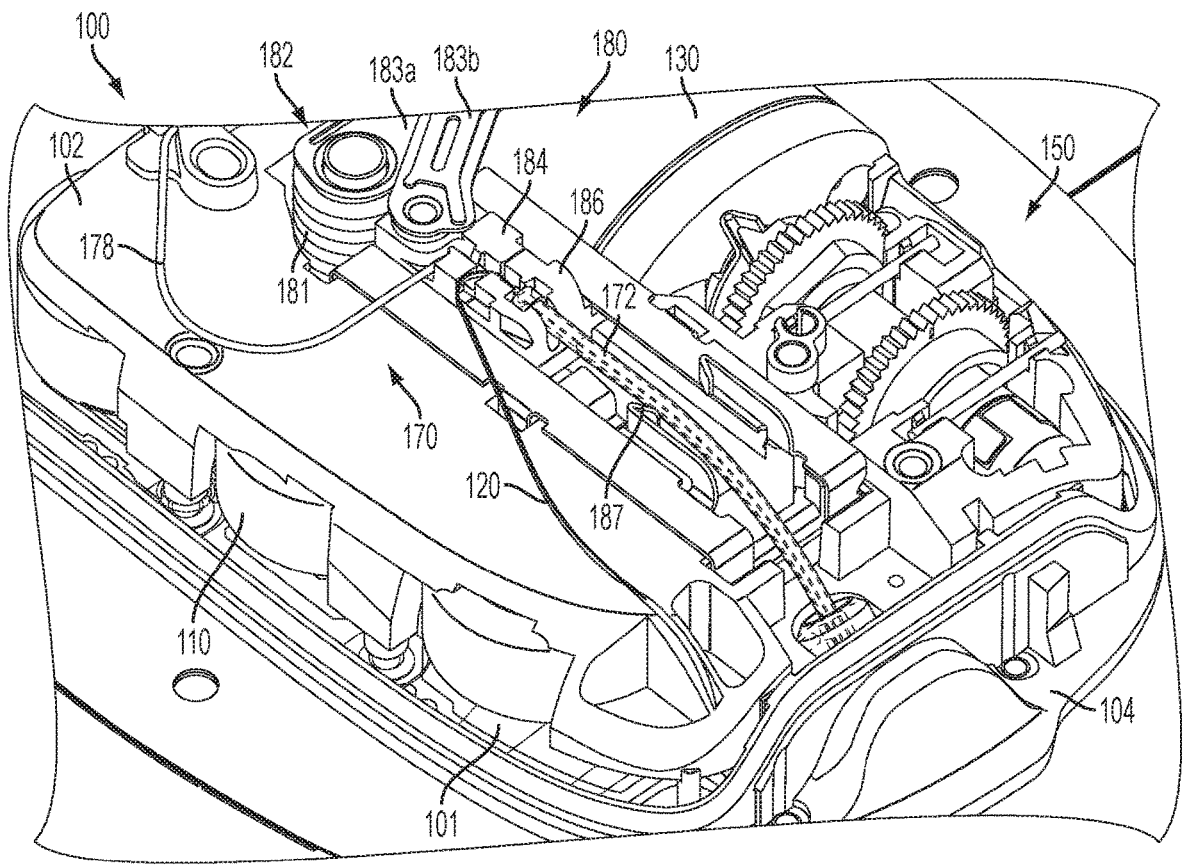
FIG. 1 is a top perspective view of a fluid delivery device with a transcutaneous access tool insertion mechanism in a pre-deployment position, consistent with the present disclosure.
FIG. 2 is a bottom perspective view of a needle and cannula retracted into the fluid delivery device in the pre-deployment position shown in FIG. 1.
Figure 3:
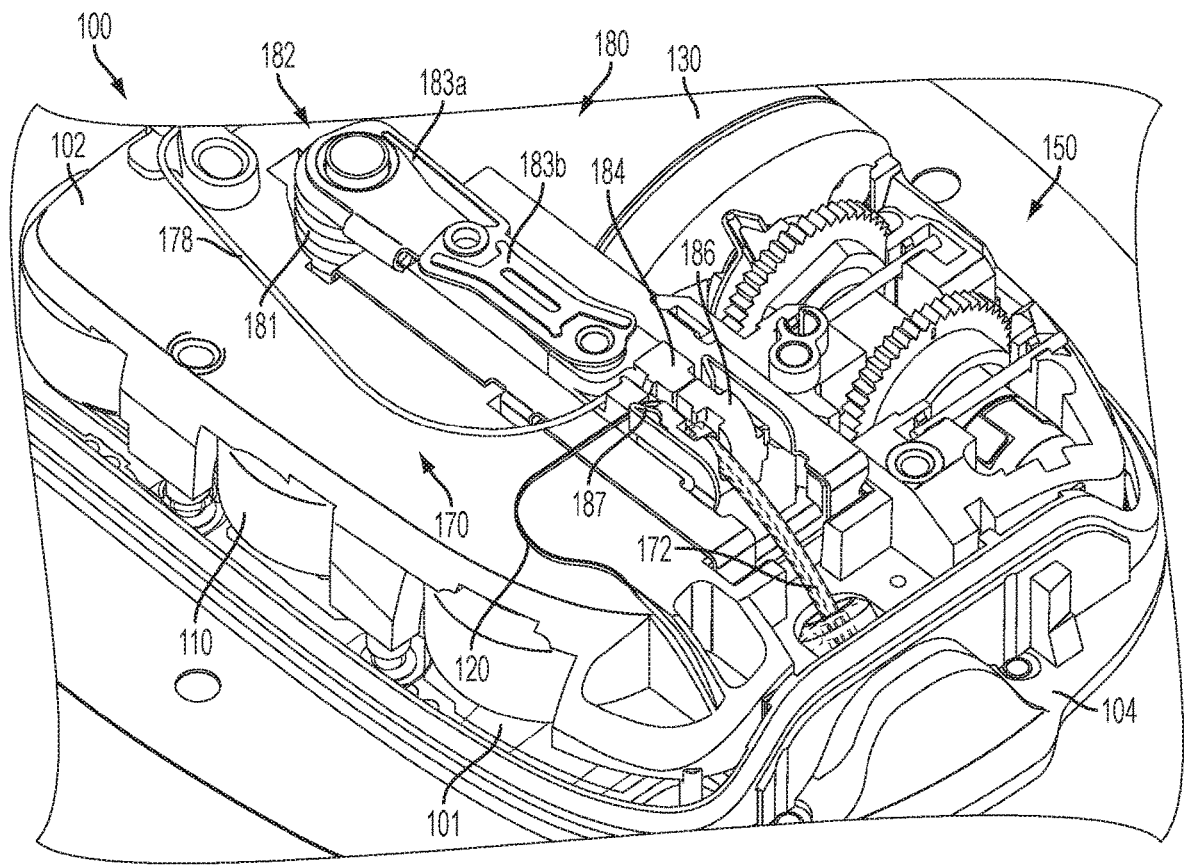
FIG. 3 is a top perspective view of the fluid delivery device shown in FIG. 1 with the insertion mechanism in an intermediate position.
Figure 4:
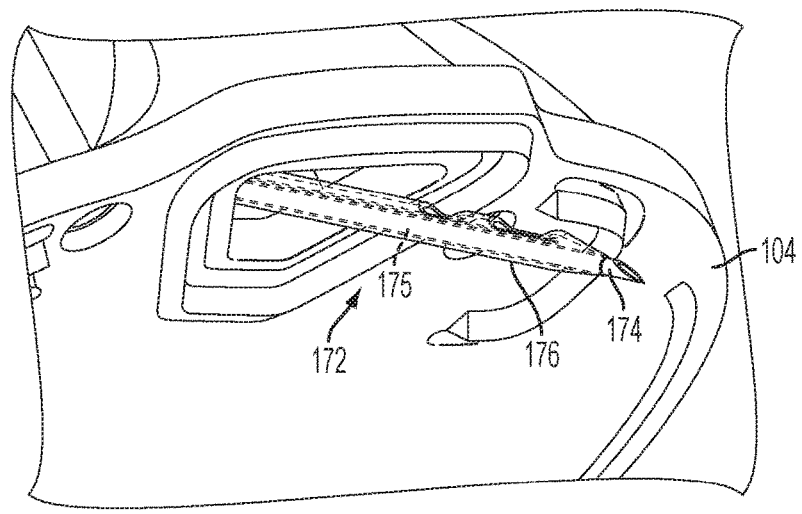
FIG. 4 is a bottom perspective view of the needle and cannula extending from the fluid delivery device in the intermediate position shown in FIG. 3.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a patient with integrated monitoring, such as continuous glucose monitoring (CGM). In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine (e.g. insulin), to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid deliver device 100. The fluid delivery device 100 may also include a housing 104 to enclose the circuit board 101, the chassis 102, and the components 110, 130, 150, 170, 180.

The fluid delivery device 100 may also include integrated monitoring such as continuous glucose monitoring (CGM). A monitor test strip 120 coupled to a monitor (not shown) in the device 100 may be introduced by the transcutaneous access tool 172 subcutaneously. One example of the monitor test strip is a CGM test strip (such as the type available from Nova Biomedical) which may be understood as a glucose sensor configured to test for a concentration level of glucose in the blood of a patient. The fluid delivery device 100 may be configured to receive data from the monitoring test strip concerning a glucose level of the patient, and determining an output of insulin from the reservoir based on the glucose level.

The transcutaneous access tool 172 includes an introducer trocar or needle 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172.

Figure 5:
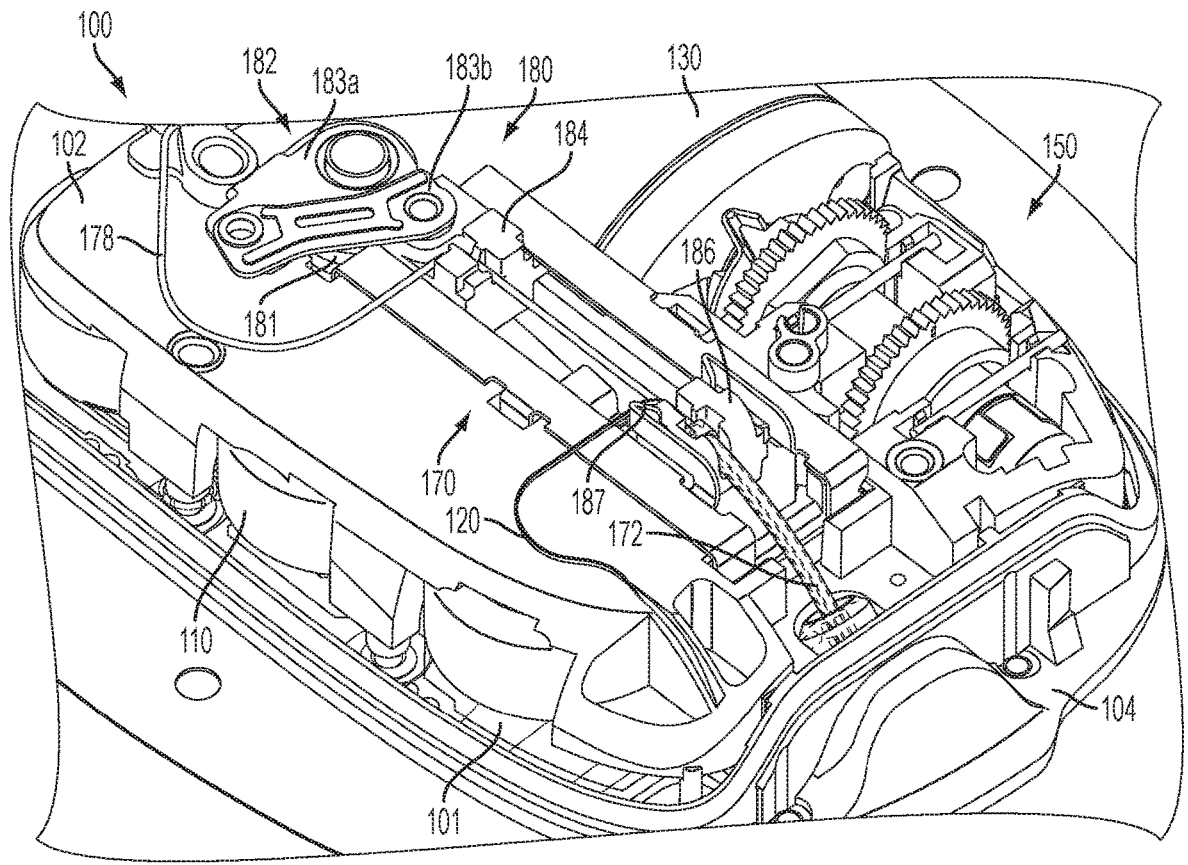
FIG. 5 is a top perspective view of the fluid delivery device shown in FIG. 1 with the insertion mechanism in a post-deployment position.
Figure 6:
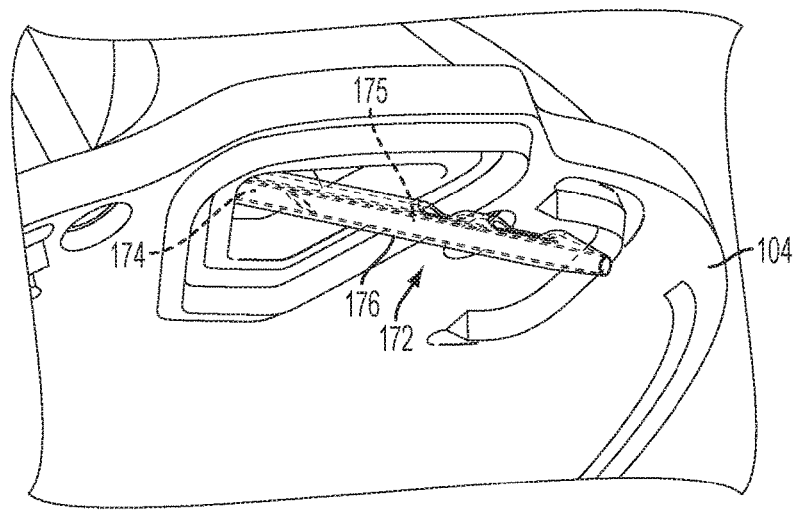
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

One embodiment of the spring-biased linkage mechanism 182 includes a helical torsion spring 181 and first and second linkages 183a, 183b coupled between the torsion spring 181 and the first sliding member 184. Energy stored in the torsion spring 181 applies a force to the linkages 183a, 183b, which applies a force to the first sliding member 184 to move the first sliding member 184 in both the insertion direction and in the retraction direction. In the pre-deployment position (FIG. 1), the torsion spring 181 is loaded and the sliding members 184, 186 are locked and prevented from moving. When the sliding members 184, 186 are released, the energy stored in the torsion spring 181 causes the first linkage 183a to rotate (e.g., clockwise as shown), which applies a force to the first sliding member 184 through the second linkage 183b causing the first sliding member 184 with the needle/trocar 174 to move (with the second sliding member 186) in the insertion direction. In the intermediate position (FIG. 3), the linkages 183a, 183b are fully extended with the needle/trocar 174 and cannula 176 being inserted, the second sliding member 186 is locked, and the remaining energy stored in the torsion spring 181 causes the first linkage 183a to continue to rotate, which applies an opposite force to the first sliding member 184 through the second linkage 183b causing the first sliding member 184 with the needle/trocar 174 to move in the retraction direction to the post-deployment position (FIG. 5). In the illustrated embodiment, the second sliding member 186 is locked against retraction by one or more latches 187. Thus, in the foregoing manner, the continuous uninterrupted clockwise rotation of first linkage 183a via the energy of torsion spring 181 provides the transcutaneous access tool insertion mechanism 180 with the ability to insert and retract the needle/trocar 174 in a single, uninterrupted motion.

The spring-biased linkage mechanism 182 allows a single spring and motion to achieve both the insertion and retraction and has a relatively small size. The spring-biased linkage mechanism 182 also reduces the static stresses caused by locking and holding back the sliding members 184, 186 and provides a smoother and more comfortable needle/trocar insertion because of the way the linkages 183a, 183b vector the forces applied to the sliding members 184, 186. The static forces on the sliding members 184, 186 are relatively small in the pre-deployment position when the linkages 183a, 183b are fully retracted. When the deployment starts and the linkages 183a, 183b start to become extended, the insertion forces increase because the force vectors increase in the insertion direction as the linkages extend 183a, 183b until a maximum insertion force is reached at the fully extended, intermediate position. By gradually increasing the insertion forces, the needle/trocar insertion and retraction is smoother, quieter and less painful.

Figure 7:
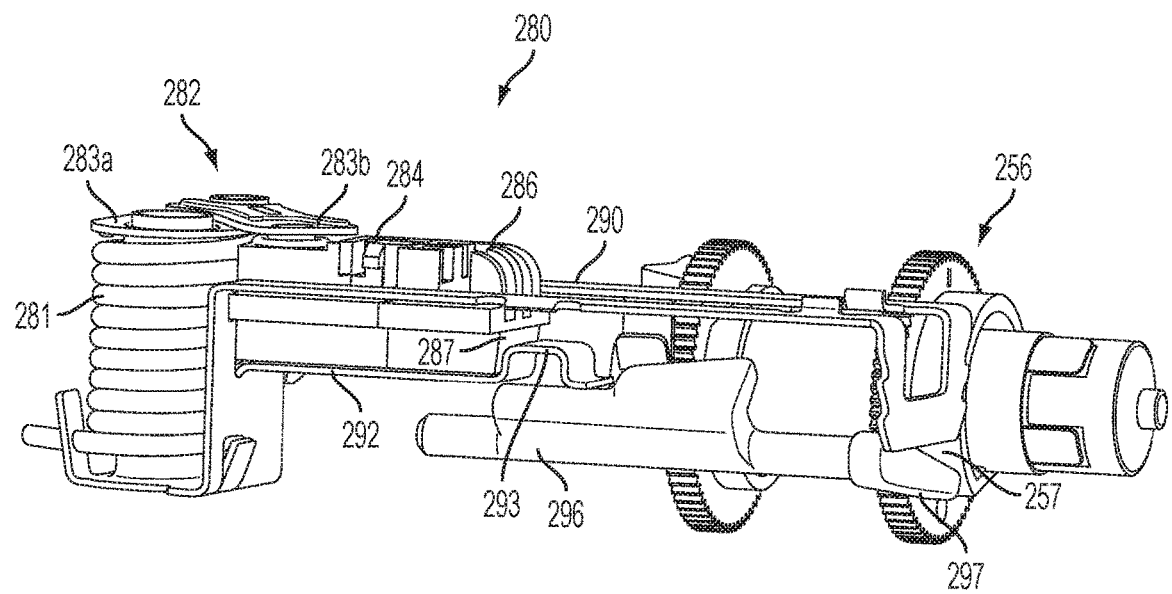
FIG. 7 is a side perspective view of another embodiment of the insertion mechanism, consistent with the present disclosure, in a pre-deployment position.
Figure 8:
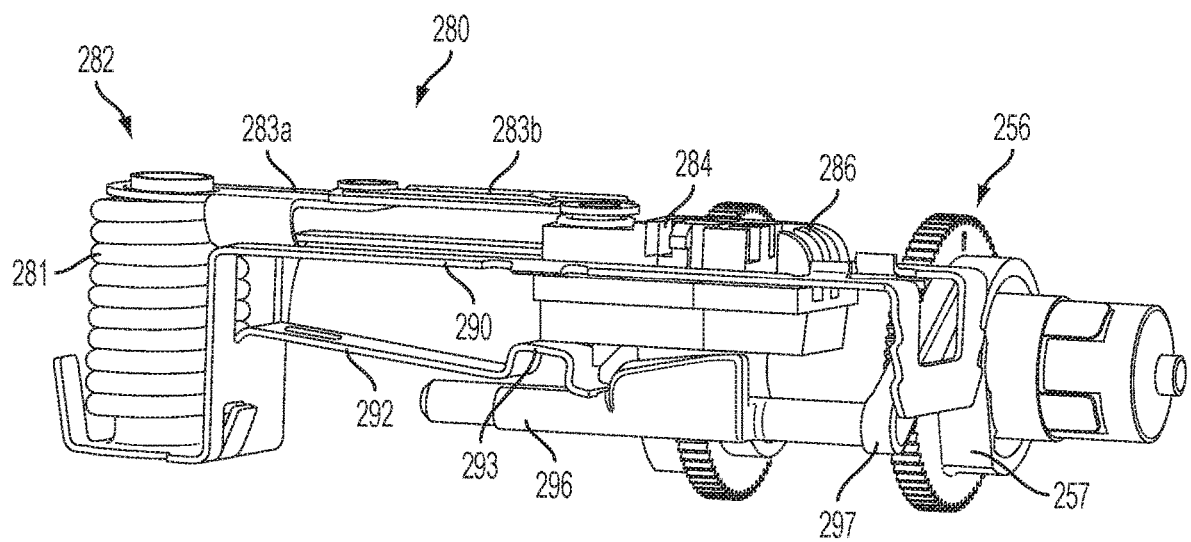
FIG. 8 is a side perspective view of the insertion mechanism shown in FIG. 7 in an intermediate position.

Another embodiment of an insertion mechanism 280 is shown in greater detail in FIGS. 7-10. The sliding members 284, 286 are slidably received in a frame 290 and moved by a spring-biased linkage mechanism 282 including torsion spring 281 and linkages 283a, 283b. In this embodiment, a cam finger 292 (e.g., extending from the frame 290) engages beneath one or both of the sliding members 284, 286 to lock the sliding members in the retracted or pre-deployment position (FIG. 7). In this pre-deployment position, the cam finger 292 is held against the sliding members 284, 286 by a release bar 296, which may be moved (rotated) to allow the cam finger 292 to move and release the sliding members 284, 286 (FIG. 8). The cam finger 292 may be biased in a downward direction and/or the second sliding member 286 may include a cam surface 287 to help facilitate movement along the cam finger 292 over locking mechanism 293 upon actuation.

The release bar 296 includes a lever 297 for pivoting the release bar 296 between an engaged position against the cam finger 292 (FIG. 7) and a disengaged position releasing the cam finger 292 (FIG. 8). The release bar 296 may be biased toward the disengaged position and held against the cam finger 292 in the engaged position until the lever 297 is released allowing the release bar 296 to move to the disengaged position. In the illustrated embodiment, the lever 297 engages a rotating surface 257 of a drive wheel 256 of the fluid drive mechanism 150 such that the lever 297 is held in the engaged position for part of the rotation and is released at a certain point during the rotation (e.g., when a flat portion of the rotating surface 257 allows the lever 297 to move).

Figure 9:
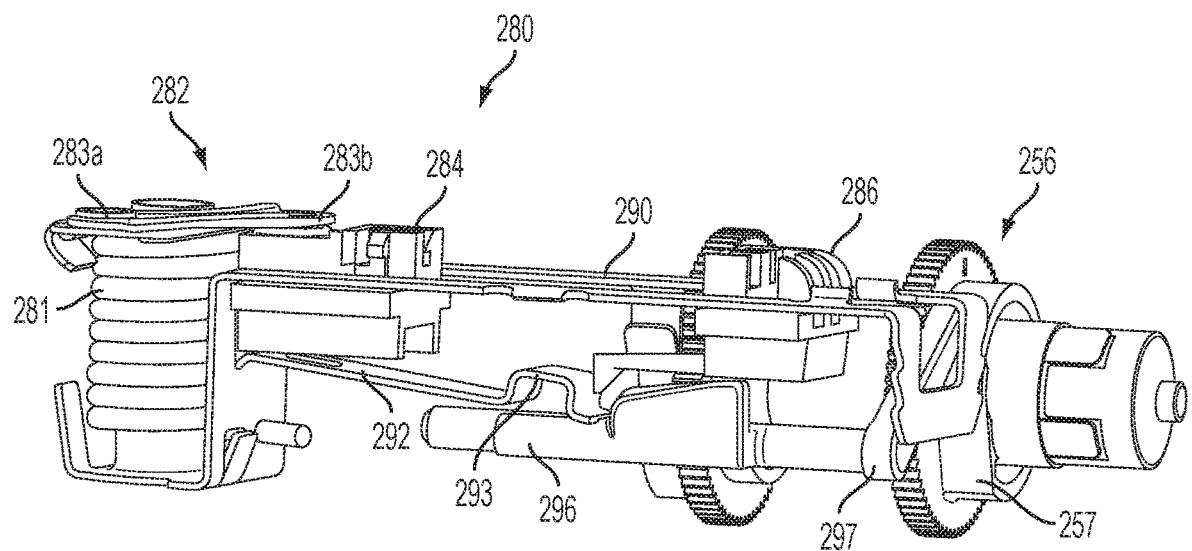
FIG. 9 is a side perspective view of the insertion mechanism shown in FIG. 7 in a post-deployment position.
Figure 10:
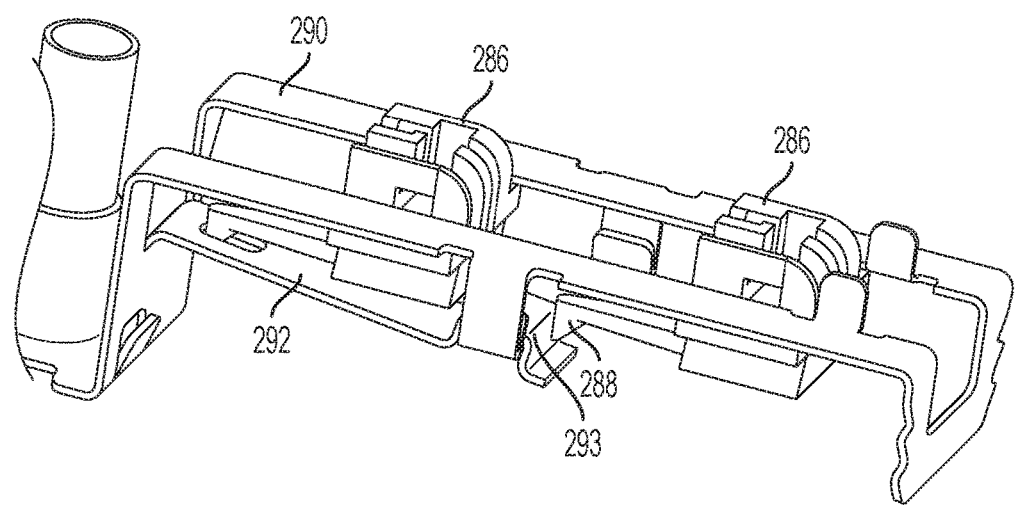
FIG. 10 is a top perspective view of the second sliding member of the insertion mechanism shown in FIG. 7 locked in the pre-deployment and post-deployment positions.

As shown in FIGS. 9 and 10, the cam finger 292 may also be used to lock the second sliding member 286 in the insertion position. A locking portion 288 of the second sliding member 286 engages a locking portion 293 of the cam finger 292 when the linkage mechanism 282 is fully extended in the intermediate position and prevents the second sliding member 286 from retracting such that the cannula remains inserted. As discussed above, the second sliding member 286 may also be locked by one or more latches 187 (shown in FIGS. 1-6) extending from a top of the frame 290.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A fluid delivery device comprising: a fluid reservoir; a transcutaneous access tool fluidly coupled to the fluid reservoir, the transcutaneous access tool including a needle or a trocar; and a transcutaneous access tool insertion and retraction mechanism, wherein the insertion and retraction mechanism comprises: a spring defining a longitudinal axis; a first linkage and a second linkage coupled between the spring and a first sliding member; the first sliding member coupled with the needle/trocar, wherein the first and second linkages configured to move the first sliding member in an insertion direction and a retraction direction in response to a force from the spring, wherein the first linkage includes a first end adjacent the spring and a second end directly coupled to the second linkage, wherein the first linkage rotates about the longitudinal axis of the spring and the second linkage rotates relative to the second end of the first linkage.

2. The fluid delivery device of claim 1 wherein the insertion and retraction mechanism is configured to increase an insertion force as the needle/trocar moves in an insertion direction.

3. The fluid delivery device of claim 1 wherein the transcutaneous access tool includes a cannula, and wherein the needle/trocar is located within the cannula such that the cannula remains inserted when the needle/trocar is retracted.

4. The fluid delivery device of claim 3 wherein the insertion and retraction mechanism comprises:
a first sliding member configured to move the needle/trocar in an insertion direction and in a retraction direction;
a second sliding member configured to move the cannula in the insertion direction;
a torsion spring; and
linkages coupled between the torsion spring and the first sliding member such that energy stored in the torsion spring causes the linkages to move the first sliding member in the insertion direction and the retraction direction.

5. The fluid delivery device of claim 4 wherein the insertion and retraction mechanism further comprises:
a frame slidably receiving the sliding members and configured to lock the sliding members in a pre-deployment position and to lock the second sliding member in a post-deployment position.

6. The fluid delivery device of claim 5 wherein the frame includes a cam finger configured to lock the sliding members in the pre-deployment position.

7. The fluid delivery device of claim 6 wherein the cam finger is configured to lock the second sliding member in the post-deployment position.

8. The fluid delivery device of claim 6 wherein the insertion and retraction mechanism further comprises:
a release bar configured to hold the cam finger when the cam finger locks the sliding members in the pre-deployment position and configured to release the cam finger to allow the sliding members to move in the insertion direction.

9. The fluid delivery device of claim 8 further comprising a drive mechanism for driving fluid from the reservoir, wherein the drive mechanism engages the release bar and triggers movement of the release bar to release the cam finger.

10. A fluid delivery device comprising:
a fluid reservoir;
a transcutaneous access tool fluidly coupled to the fluid reservoir, the transcutaneous access tool including a cannula, and a needle or a trocar located inside the cannula;
a transcutaneous access tool insertion and retraction mechanism configured to deploy the transcutaneous access tool, comprising
a first sliding member coupled with the needle/trocar and operable to move the needle/trocar in an insertion direction and in a retraction direction;
a second sliding member coupled with the cannula and operable to move the cannula in the insertion direction;
a torsion spring;
linkages coupled between the torsion spring and the first sliding member such that energy stored in the torsion spring causes the linkages to move the first sliding member in the insertion direction and the retraction direction; and
wherein the torsion spring has a longitudinal axis and the linkages rotate around the longitudinal axis of the torsion spring.

11. The fluid delivery device of claim 10 wherein the transcutaneous access tool insertion and retraction mechanism is configured to insert the needle/trocar with an increasing insertion force as the needle/trocar moves in an insertion direction; and
wherein the torsion spring operates to increase the insertion force as the needle/trocar moves in the insertion direction.

12. The fluid delivery device of claim 10 wherein the needle/trocar is located within the cannula such that the cannula remains inserted when the needle/trocar is retracted.

13. The fluid delivery device of claim 10 wherein the insertion and retraction mechanism further comprises:
a frame slidably receiving the sliding members and configured to lock the sliding members in a pre-deployment position and to lock the second sliding member in a post-deployment position.

14. The fluid delivery device of claim 13 wherein the frame includes a cam finger configured to lock the sliding members in the pre-deployment position.

15. The fluid delivery device of claim 14 wherein the cam finger is configured to lock the second sliding member in the post-deployment position.

16. The fluid delivery device of claim 14 wherein the insertion and retraction mechanism further comprises:
a release bar configured to hold the cam finger when the cam finger locks the sliding members in the pre-deployment position and configured to release the cam finger to allow the sliding members to move in the insertion direction.

17. The fluid delivery device of claim 16 further comprising a drive mechanism for driving fluid from the reservoir, wherein the drive mechanism engages the release bar and triggers movement of the release bar to release the cam finger.

18. A transcutaneous access tool insertion and retraction mechanism configured to deploy a transcutaneous access tool including a cannula, and a needle or a trocar located inside of the cannula, the insertion and retraction mechanism comprising:
a first sliding member coupled with the needle/trocar and operable to move the needle/trocar in an insertion direction and in a retraction direction;
a second sliding member coupled with the cannula and operable to move the cannula in the insertion direction;
a torsion spring having a longitudinal axis;
first and second linkages coupled between the torsion spring and the first sliding member such that, upon deployment, energy stored in the torsion spring causes the first and second linkages to cooperate to move the first sliding member in the insertion direction and the retraction direction; and
wherein, upon deployment, the first linkage is arranged to rotate about the longitudinal axis of the torsion spring, and the first linkage and second linkage are arranged to rotate relative to each other about a moving pivot to move the first sliding member in the insertion direction and the retraction direction.

19. The transcutaneous access tool insertion and retraction mechanism of claim 18 further comprising:
a frame slidably receiving the sliding members and configured to lock the sliding members in a pre-deployment position and to lock the second sliding member in a post-deployment position.

20. The transcutaneous access tool insertion and retraction mechanism of claim 19 wherein the frame includes a cam finger configured to lock the sliding members in the pre-deployment position.

21. The transcutaneous access tool insertion and retraction mechanism of claim 20 wherein the cam finger is configured to lock the sliding members in the post-deployment position.

22. The transcutaneous access tool insertion and retraction mechanism of claim 20 further comprising:
a release bar configured to hold the cam finger when the cam finger locks the sliding members in the pre-deployment position and configured to release the cam finger to allow the sliding members to move in the insertion direction.

* * * * *